US012005253B2

(12) United States Patent
Avigdor et al.

(10) Patent No.: US 12,005,253 B2
(45) Date of Patent: Jun. 11, 2024

(54) COMPOSITIONS AND METHODS FOR INCREASING CANCER CELL SENSITIVITY TO ALTERNATING ELECTRIC FIELDS

(71) Applicant: Novocure GMBH, Root (CH)

(72) Inventors: Lilach Avigdor, Haifa (IL); Tali Voloshin-Sela, Haifa (IL)

(73) Assignee: NOVOCURE GMBH, Root (CH)

( * ) Notice: Subject to any disclaimer, the term of this patent is extended or adjusted under 35 U.S.C. 154(b) by 18 days.

(21) Appl. No.: 17/841,968

(22) Filed: Jun. 16, 2022

(65) Prior Publication Data

US 2023/0001193 A1 Jan. 5, 2023

Related U.S. Application Data

(60) Provisional application No. 63/235,620, filed on Aug. 20, 2021, provisional application No. 63/216,964, filed on Jun. 30, 2021.

(51) Int. Cl.
*A61K 45/06* (2006.01)
*A61N 1/36* (2006.01)

(52) U.S. Cl.
CPC .......... *A61N 1/36002* (2017.08); *A61K 45/06* (2013.01)

(58) Field of Classification Search
CPC .. A61N 1/36002; A61N 1/0476; A61K 45/06; A61K 31/416
See application file for complete search history.

(56) References Cited

U.S. PATENT DOCUMENTS

2017/0290916 A1* 10/2017 Kaushik ............. A61K 47/6923
2020/0297286 A1* 9/2020 Costa ................... A61B 5/7292

(Continued)

OTHER PUBLICATIONS

Klein-Goldberg, et al., "Targeting Akt Signaling Pathway Potentiates the Antitumor Effect of Tumor Treating Fields (TTFields) in Vitro," Cancer Research (Jul. 31, 2021).

(Continued)

*Primary Examiner* — Ankit D Tejani
*Assistant Examiner* — Joshua Brendon Solomon
(74) *Attorney, Agent, or Firm* — BALLARD SPAHR LLP

(57) ABSTRACT

Disclosed herein are methods of increasing sensitivity of a cancer cell to alternating electric fields comprising exposing the cancer cell to an alternating electric field for a period of time, the alternating electric field having a frequency and field strength, and exposing the cancer cell to an IGFR1 inhibitor, JNK inhibitor, RPS6 inhibitor or ERK inhibitor. Disclosed are methods of increasing treatment efficacy comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject. Disclosed are methods of treating a subject having cancer comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject. Disclosed are methods of reducing viability of cancer cells using an alternating electric field for a period of time, the alternating electric field having a frequency and field strength in combination with either an IGF1R inhibitor, JNK inhibitor, RPS6 inhibitor, and/or ERK inhibitor. Disclosed are methods of increasing apoptosis of a cancer cell comprising exposing the cancer cell to an alternating electric field for a period of time, the alternating electric field having a frequency and field strength; and exposing the cancer cell to an IGFR1 inhibitor, JNK inhibitor, RPS6 inhibitor or ERK inhibitor.

15 Claims, 3 Drawing Sheets

(56) References Cited

U.S. PATENT DOCUMENTS

| | | |
|---|---|---|
| 2021/0038584 A1 | 2/2021 | Voloshin-Sela |
| 2021/0178155 A1 | 6/2021 | Hershkovich et al. |
| 2021/0178173 A1 | 6/2021 | Hershkovich et al. |
| 2022/0096818 A1* | 3/2022 | Voloshin-Sela .... A61K 31/5377 |

OTHER PUBLICATIONS

Voloshin, T., et al., "Safety and Effectiveness of Tumor Treating Fields (TTFields; 150 kHz) and Sorafenib Combination Treatment in Hepatocellular Carcinoma In Vitro and In Vivo," International Journal of Radition: Oncology Biology Physics, Pergamon Press, vol. 108(3) (Nov. 1, 2020).

Written Opinion and International Search Report mailed Aug. 30, 2022 in PCT/IB2022/055589 filed Jun. 16, 2022 (13 pages).

U.S. Appl. No. 63/216,964, filed Jun. 30, 2021, Avigdor (Novocure GMBH).

U.S. Appl. No. 63/235,620, filed Aug. 20, 2021, Avigdor (Novocure GMBH).

PCT/IB2022/055589, filed Aug. 30, 2022, Avigdor (Novocure GMBH).

* cited by examiner

COMPOSITIONS AND METHODS FOR INCREASING CANCER CELL SENSITIVITY TO ALTERNATING ELECTRIC FIELDS

CROSS-REFERENCE TO RELATED APPLICATIONS

This application claims benefit of U.S. Provisional Application No. 63/216,964 filed Jun. 30, 2021, AND U.S. Application No. 63/235,620. Filed Aug. 20, 2021 each of which are hereby incorporated herein by reference in their entirety.

BACKGROUND

Tumor Treating Fields, or TTFields, are low intensity (e.g., 1-3 V/cm) alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. TTFields are FDA approved for the treatment of glioblastoma (GBM), and may be delivered, for example, via the Optune™ system. Optune™ includes a field generator and two pairs of transducer arrays (i.e., electrode arrays) that are placed on a patient's shaved head. One pair of electrodes is positioned to the left and right of the tumor, and the other pair of electrodes is positioned anterior and posterior to the tumor. In the preclinical setting, TTFields can be applied in vitro using, for example, the Inovitro™ TTFields lab bench system.

TTFields therapy is an approved mono-treatment for recurrent glioblastoma, and an approved combination therapy with chemotherapy for newly diagnosed glioblastoma and unresectable malignant pleural mesothelioma patients. These electric fields are induced non-invasively by transducer arrays (i.e., arrays of electrodes) placed directly on the patient's scalp. TTFields also appear to be beneficial for treating tumors in other parts of the body.

Disclosed herein are combination therapies using alternating electric fields (e.g. a TTField) and one or more of an IGFR1 inhibitor, JNK inhibitor, RPS6 inhibitor or ERK inhibitor to help increase a cancer cells sensitivity to alternating electric fields.

BRIEF SUMMARY

Disclosed are methods of increasing sensitivity of a cancer cell to alternating electric fields comprising exposing the cancer cell to an alternating electric field for a period of time, the alternating electric field having a frequency and field strength, and exposing the cancer cell to an IGFR1 inhibitor, JNK inhibitor, RPS6 inhibitor or ERK inhibitor.

Disclosed are methods of increasing treatment efficacy comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject.

Disclosed are methods of treating a subject having cancer comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject.

Disclosed are methods of reducing viability of cancer cells using an alternating electric field for a period of time, the alternating electric field having a frequency and field strength in combination with either an IGF1R inhibitor, JNK inhibitor, RPS6 inhibitor, and/or ERK inhibitor.

Disclosed are methods of increasing apoptosis of a cancer cell comprising exposing the cancer cell to an alternating electric field for a period of time, the alternating electric field having a frequency and field strength; and exposing the cancer cell to an IGFR1 inhibitor, JNK inhibitor, RPS6 inhibitor or ERK inhibitor.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
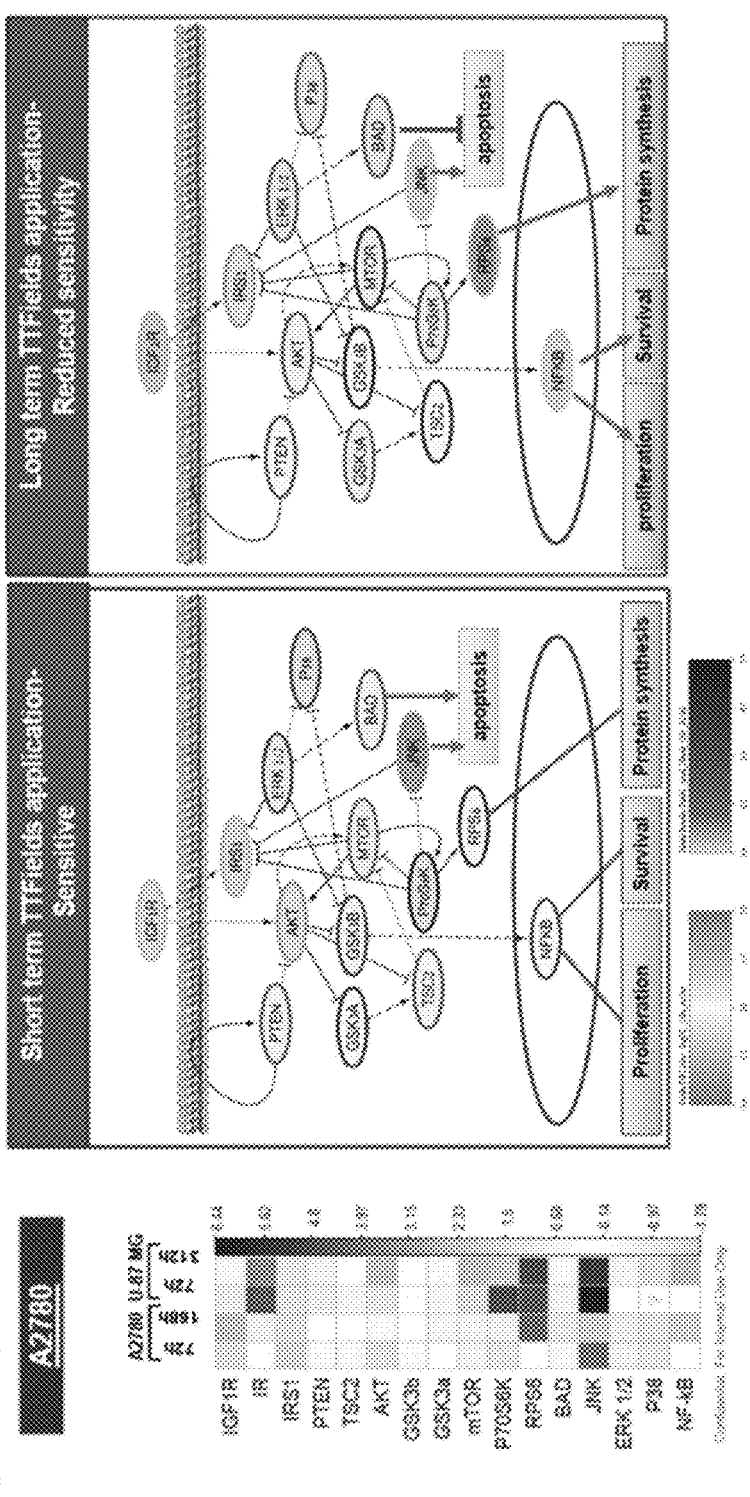
FIG. 1 is results from a Luminex analysis showing changes in protein expression in A2780 (ovarian cancer cell line): Short term (left) is showing protein expression changes in TTFields following 72 hours compared with control samples results. Long term (right) is showing protein expression changes in TTFields following 168 hours compared with control samples results. Colors inside the circle-legend on the left bottom part of the figure—the darker colors towards the top of the scale show increase in expression, the lighter colors towards the bottom of the scale show a decrease in expression and no color shows no change. The surrounding lines of circles-legend on the right bottom part of the figure—the degree of statistically significant. Straight lines show a direct connection between proteins while dotted lines show an indirect connection.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. DEFINITIONS

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a JNK inhibitor" or "an ERK inhibitor" includes a plurality of such JNK or ERK inhibitors, reference to "the cancer cell" is a reference to one or more cancer cells and equivalents thereof known to those skilled in the art, and so forth.

As used herein, an "alternating electric field" or "alternating electric fields" refers to a very-low-intensity, directional, intermediate-frequency alternating electrical fields delivered to a subject, a sample obtained from a subject or to a specific location within a subject or patient (e.g. a target site). In some aspects, the alternating electrical field can be in a single direction or multiple directional. In some aspects, alternating electric fields can be delivered through two pairs of transducer arrays that generate perpendicular fields within the treated heart. For example, for the Optune™ system (an alternating electric fields delivery system) one pair of electrodes is located to the left and right (LR) of the heart, and the other pair of electrodes is located anterior and posterior (AP) to the heart. Cycling the field between these two directions (i.e., LR and AP) ensures that a maximal range of cell orientations is targeted. In some aspects, an alternating electric field can be referred to as Tumor Treating Field (TTF).

In-vivo and in-vitro studies show that the efficacy of alternating electric fields therapy increases as the intensity of the electrical field increases. Therefore, optimizing array placement on the area of a patient's tumor to increase the intensity in the desired region of the tumor can be performed with the Optune system. Array placement optimization may be performed by "rule of thumb" (e.g., placing the arrays on the tumor as close to the desired region of the target site (e.g. cancer cells) as possible), measurements describing the geometry of the patient's tumor, tumor dimensions. Measurements used as input may be derived from imaging data. Imaging data is intended to include any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electrical field distributes within the head as a function of the positions of the array and, in some aspects, take account for variations in the electrical property distributions within the heads of different patients.

The term "subject" refers to the target of administration, e.g. an animal. Thus, the subject of the disclosed methods can be a vertebrate, such as a mammal. For example, the subject can be a human. The term does not denote a particular age or sex. Subject can be used interchangeably with "individual" or "patient." For example, the subject of administration can mean the recipient of the alternating electrical field.

By "treat" is meant to administer or apply a therapeutic, such as alternating electric fields, to a subject, such as a human or other mammal (for example, an animal model), that has cancer or has an increased susceptibility for developing cancer, in order to prevent or delay a worsening of the effects of the cancer, or to partially or fully reverse the effects of the cancer (glioblastoma, ovarian, or lung metastatic carcinoma).

By "prevent" is meant to minimize the chance that a subject who has an increased susceptibility for developing cancer will develop cancer.

As used herein, the terms "administering" and "administration" refer to any method of providing a therapeutic, such as an IGFR1 inhibitor, JNK inhibitor, RPS6 inhibitor or ERK inhibitor to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration so as to treat a subject. In some aspects, administering comprises exposing. Thus, in some aspects, exposing a cancer cell to alternating electrical fields means administering alternating electrical fields to the cancer cell.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. METHODS OF INCREASING SENSITIVITY

In some aspects, alternating electric fields can increase expression of certain genes. For example, application of an alternating electric fields to a cell or subject can increase expression of genes such as IGF1R, JNK, RPS6, and ERK in the cell or subject.

The insulin-like growth factor 1 (IGF-1) receptor is a protein found on the surface of human cells. It is a transmembrane receptor that is activated by a hormone called insulin-like growth factor 1 (IGF-1) and by a related hormone called IGF-2. It belongs to the large class of tyrosine kinase receptors. This receptor mediates the effects of IGF-1, which is a polypeptide protein hormone similar in molecular structure to insulin. IGF-1 plays an important role in growth and continues to have anabolic effects in adults—meaning that it can induce hypertrophy of skeletal muscle and other target tissues. Mice lacking the IGF-1 receptor die late in development, and show a dramatic reduction in body mass. The IGF-1R is implicated in several cancers, including breast, prostate, and lung cancers. In some instances, its anti-apoptotic properties allow cancerous cells to resist the cytotoxic properties of chemotherapeutic drugs or radiotherapy. In breast cancer, where EGFR inhibitors such as erlotinib are being used to inhibit the EGFR signaling pathway, IGF-1R confers resistance by forming one half of a heterodimer (see the description of EGFR signal transduction in the erlotinib page), allowing EGFR signaling to resume in the presence of a suitable inhibitor. This process is referred to as crosstalk between EGFR and IGF-1R. It is further implicated in breast cancer by increasing the metastatic potential of the original tumor by conferring the ability to promote vascularization.

Increased levels of the IGF-IR are expressed in the majority of primary and metastatic prostate cancer patient tumors. Evidence suggests that IGF-IR signaling is required for survival and growth when prostate cancer cells progress to androgen independence. In addition, when immortalized prostate cancer cells mimicking advanced disease are treated with the IGF-1R ligand, IGF-1, the cells become more motile. Members of the IGF receptor family and their ligands also seem to be involved in the carcinogenesis of mammary tumors of dogs. IGF1R is amplified in several cancer types based on analysis of TCGA data, and gene amplification could be one mechanism for overexpression of IGF in cancer.

c-Jun N-terminal kinases (JNKs), were originally identified as kinases that bind and phosphorylate c-Jun on Ser-63 and Ser-73 within its transcriptional activation domain. They belong to the mitogen-activated protein kinase family, and are responsive to stress stimuli, such as cytokines, ultraviolet irradiation, heat shock, and osmotic shock. They also play a role in T cell differentiation and the cellular apoptosis pathway. Activation occurs through a dual phosphorylation of threonine (Thr) and tyrosine (Tyr) residues within a Thr-Pro-Tyr motif located in kinase subdomain VIII. Activation is carried out by two MAP kinase kinases, MKK4 and MKK7, and JNK can be inactivated by Ser/Thr and Tyr protein phosphatases. It has been suggested that this signaling pathway contributes to inflammatory responses in mammals and insects.

JNK, by phosphorylation, modifies the activity of numerous proteins that reside at the mitochondria or act in the nucleus. Downstream molecules that are activated by JNK include c-Jun, ATF2, ELK1, SMAD4, p53 and HSF1. The downstream molecules that are inhibited by JNK activation include NFAT4, NFATC1 and STAT3. By activating and inhibiting other small molecules in this way, JNK activity regulates several important cellular functions including cell growth, differentiation, survival and apoptosis. JNK activation is involved in tumorigenesis of several cancer types.

Ribosomal protein S6 (rpS6 or eS6) is a component of the 40S ribosomal subunit and is therefore involved in translation. Mouse model studies have shown that phosphorylation of eS6 is involved in the regulation of cell size, cell proliferation, and glucose homeostasis.

Extracellular signal-regulated kinases (ERKs) or classical MAP kinases are widely expressed protein kinase intracellular signaling molecules that are involved in functions including the regulation of meiosis, mitosis, and postmitotic functions in differentiated cells. Many different stimuli, including growth factors, cytokines, virus infection, ligands for heterotrimeric G protein-coupled receptors, transforming agents, and carcinogens, activate the ERK pathway. Disruption of the ERK pathway is common in cancers, especially Ras, c-Raf, and receptors such as HER2. ERK can also activate pro-survival pathways in tumors.

Activation of the ERK1/2 pathway by aberrant RAS/RAF signaling, DNA damage, and oxidative stress leads to cellular senescence. Low doses of DNA damage resulting from cancer therapy cause ERK1/2 to induce senescence, whereas higher doses of DNA damage fail to activate ERK1/2, and thus induce cell death by apoptosis.

As provided herein, decreasing or inhibiting expression of one or more of IGF1R, JNK, RPS6, and ERK can allow for prolonged use or application of alternating electric fields to a cell or subject or can allow for increased frequency or field strength applied to a cell or subject. Also provided herein, decreasing or inhibiting expression of one or more of IGF1R, JNK, RPS6, and ERK can prolong survival and enhance efficacy of TTFields treatment. Prolonging the use of TTFields seems less relevant.

Because alternating electric fields can be used to treat several diseases and disorders, for example, as a cancer therapeutic, reducing or preventing any negative side effects (such as activation of transcriptional and proteasomal pathways that could lead to disease progression or reduced survival) from the alternating electric fields can help increase the sensitivity of a cell or subject to the alternating electric fields. Disclosed are methods of increasing sensitivity of a cancer cell to alternating electric fields comprising exposing the cancer cell to an alternating electric field for a period of time, the alternating electric field having a frequency and field strength, and exposing the cancer cell to a IGF1R inhibitor, JNK inhibitor, RPS6 inhibitor, and/or an ERK inhibitor. Also, disclosed are methods of increasing sensitivity of a cell to alternating electric fields comprising exposing the cell to an alternating electric field for a period of time, the alternating electric field having a frequency and field strength, and exposing the cell to a IGF1R inhibitor, JNK inhibitor, RPS6 inhibitor, and/or an ERK inhibitor. In some aspects, the cell or cancer cell are in a subject and exposing the cell to a IGF1R inhibitor, JNK inhibitor, RPS6 inhibitor, and/or an ERK inhibitor increases the subject's sensitivity to alternating electric fields.

In some aspects, alternating electric fields can increase expression of IGF1R. Overexpression of IGFR1 can induce cancer growth. Because alternating electric fields can be used to treat several diseases and disorders, for example, as a cancer therapeutic, reducing or preventing any negative side effects from the alternating electric fields can help increase the sensitivity of the alternating electric fields, thus decreasing or inhibiting expression of expression of IGF1R caused by alternating electric fields can increase the sensitivity of the alternating electric fields.

In some aspects, the IGFR1 inhibitors can be, but are not limited to, antibodies, small molecules, oligonucleotides. In some aspects, the antibodies can be monoclonal antibodies against IFG1R or monoclonal antibodies against IFG1R ligand. In some aspects, the small molecules can be IGF1R tyrosine kinase inhibitors. In some aspects, the oligonucleotides can be antisense oligonucleotides, RNA interference, or circular RNA. In some aspects, the IGFR1 inhibitor can be selected from, but is not limited to, one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), 5961. Thus, disclosed are methods of increasing sensitivity of a cancer cell to alternating electric fields comprising exposing the cancer cell to an alternating electric field for a period of time, the alternating electric field having a frequency and field strength, and exposing the cancer cell to an IGF1R inhibitor. Also disclosed are methods of increasing sensitivity of a cell to alternating electric fields comprising exposing the cell to an alternating electric field for a period of time, the alternating electric field having a frequency and field strength, and exposing the cell to an IGF1R inhibitor. In some aspects, the cell or cancer cell are in a subject.

In some aspects, the JNK inhibitors can be, but are not limited to, SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines. Thus, also disclosed are methods of increasing sensitivity of a cancer cell to alternating electric fields comprising exposing the cancer cell to an alternating electric field for a period of time, the alternating electric field having a frequency and field strength, and exposing the cancer cell to a JNK inhibitor. Also disclosed are methods of increasing sensitivity of a cell to alternating electric fields comprising exposing the cell to an alternating electric field for a period of time, the alternating electric field having a frequency and field strength, and exposing the cell to a JNK inhibitor.

In some aspects, an RPS6 inhibitor can be any composition or compound that inhibits RPS6, inhibits phosphorylation of RPS6, or inhibits phosphorylated RPS6. In some aspects, a RPS6 inhibitor can be, a shRNA. In some aspects, a RPS6 inhibitor can be an mTOR inhibitor, wherein mTOR inhibitors act as a dephosphorylator of RPS6. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D and TML-6. In some aspects, a RPS6 inhibitor can be an AKT inhibitor, wherein AKT inhibitors act can prevent RPS6 phosphorylation. In some aspects, an AKT inhibitor can be, but is not limited to, lapatinib, H 8, H 89, NL 71.101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, or NSC781406. Thus, also disclosed are methods of increasing sensitivity of a cancer cell to alternating electric fields comprising exposing the cancer cell to an alternating electric field for a period of time, the alternating electric field having a frequency and field strength, and exposing the cancer cell to a RPS6 inhibitor. Also disclosed are methods of increasing sensitivity of a cell to alternating electric fields comprising exposing the cell to an alternating electric field for a period of time, the alternating electric field having a frequency and field strength, and exposing the cell to a RPS6 inhibitor. In some aspects, the cell or cancer cell are in a subject.

In some aspects, the ERK inhibitor can be selected from, but is not limited to, one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, trans-zeatin, AZD0364, usnic acid, ASTX-029, VX-11e, notoginsenoside R1, CC-90003, 2'S'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994). Because ERK is the only substrate of MEK, in some aspects, an ERK inhibitor can be an inhibitor of an element upstream of ERK, such as a MEK inhibitor. Examples of MEK inhibitors can be, but are not limited to, selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, RO5126766, GDC-0623. Thus, also disclosed are methods of increasing sensitivity of a cancer cell to alternating electric fields comprising exposing the cancer cell to an alternating electric field for a period of time, the alternating electric field having a frequency and field strength, and exposing the cancer cell to an ERK inhibitor. Also disclosed are methods of increasing sensitivity of a cell to alternating electric fields comprising exposing the cell to an alternating electric field for a period of time, the alternating electric field having a frequency and field strength, and exposing the cell to an ERK inhibitor. In some aspects, the cell or cancer cell are in a subject.

In some aspects, the cancer cell is a glioblastoma cell, ovarian cell, or lung metastatic carcinoma cell. In some aspects, the cancer cell can be from any cancer.

In some aspects, the cancer cell is in a subject. Thus, in some aspects, exposing the cancer cell to an alternating electric field for a period of time comprises applying the alternating electric field to the subject in an area comprising the cancer cells. For example, if the cancer cell is a glioblastoma cell then the alternating electric field can be applied to the head of the subject.

In some aspects, the cancer cells are exposed to the alternating electric field and an IGFR1 inhibitor, JNK inhibitor, RPS6 inhibitor or ERK inhibitor simultaneously. In some aspects, the cancer cells are exposed to the alternating electric field and IGFR1 inhibitor, JNK inhibitor, RPS6 inhibitor or ERK inhibitor consecutively. In some aspects, the cancer cells are exposed to the alternating electric field just prior to or just after IGFR1 inhibitor, JNK inhibitor, RPS6 inhibitor or ERK inhibitor administration.

Disclosed are any of the above methods of increasing sensitivity of a cancer cell to alternating electric fields comprising exposing the cancer cell to an alternating electric field for a period of time, the alternating electric field having a frequency and field strength, and exposing the cancer cell to an IGFR1 inhibitor, JNK inhibitor, RPS6 inhibitor or ERK inhibitor and further comprising exposing the cell to a chemotherapeutic agent, an anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin). In some aspects, a chemotherapeutic agent can be, but is not limited to, an alkylating agent, an antimetabolite agent, an antineoplastic antibiotic agent, a mitotic inhibitor agent. In some aspects, the methods can further comprise exposing a cell to radiation therapy. In some aspects, the methods can further comprise exposing a cell to an immuno-oncology agent. In some aspects, an immune-oncology agent can be, but is not limited to, immune checkpoint inhibitors such as, Ipilimumab, Nivolumab, Pembrolizumab, Atezolizumab, Avelumab, and Durvalumab. In some aspects, these categories of agents and therapeutics are overlapping, for example, Pebrolizumab is an immune-oncology agent and also considered an antineoplastic agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the alternating electric fields. In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the IGFR1 inhibitor, JNK inhibitor, RPS6 inhibitor or ERK inhibitor.

C. METHODS OF TREATING

Disclosed are methods of increasing treatment efficacy comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject.

Disclosed are methods of treating a subject having cancer comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject.

In some aspects, the one or more of the IGF1R inhibitor, JNK inhibitor, RPS6 inhibitor, or ERK inhibitor is administered prior to applying the alternating electric field. In some aspects, the one or more of the IGF1R inhibitor, JNK inhibitor, RPS6 inhibitor, or ERK inhibitor is administered after applying the alternating electric field. In some aspects, the one or more of the IGF1R inhibitor, JNK inhibitor, RPS6 inhibitor, or ERK inhibitor is administered simultaneously with applying the alternating electric field.

In some aspects, the cancer is a glioblastoma, ovarian, or lung metastatic carcinoma. In some aspects, the cancer can be any cancer.

In some aspects, the IGFR1 inhibitors can be, but are not limited to, antibodies, small molecules, oligonucleotides. In some aspects, the antibodies can be monoclonal antibodies against IFG1R or monoclonal antibodies against IFG1R ligand. In some aspects, the small molecules can be IGF1R tyrosine kinase inhibitors. In some aspects, the oligonucleotides can be antisense oligonucleotides, RNA interference, or circular RNA. In some aspects, the IGFR1 inhibitor can be selected from, but is not limited to, one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), 5961. Thus, disclosed are methods of increasing sensitivity of a cancer cell to alternating electric fields comprising exposing the cancer cell to an alternating electric field for a period of time, the alternating electric field having a frequency and field strength, and exposing the cancer cell to an IGF1R inhibitor.

In some aspects, the JNK inhibitors can be, but are not limited to, SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines. Thus, also disclosed are methods of increasing sensitivity of a cancer cell to alternating electric fields comprising exposing the cancer cell to an alternating electric field for a period of time, the alternating electric field having a frequency and field strength, and exposing the cancer cell to a JNK inhibitor.

In some aspects, an RPS6 inhibitor can be any composition or compound that inhibits RPS6, inhibits phosphorylation of RPS6, or inhibits phosphorylated RPS6. In some aspects, a RPS6 inhibitor can be, a shRNA. In some aspects, a RPS6 inhibitor can be an mTOR inhibitor, wherein mTOR inhibitors act as a dephosphorylator of RPS6. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D and TML-6. In some aspects, a RPS6 inhibitor can be an AKT inhibitor, wherein AKT inhibitors act can prevent RPS6 phosphorylation. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f] [1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, or NSC781406. Thus, also disclosed are methods of increasing sensitivity of a cancer cell to alternating electric fields comprising exposing the cancer cell to an alternating electric field for a period of time, the alternating electric field having a frequency and field strength, and exposing the cancer cell to a RPS6 inhibitor.

In some aspects, the ERK inhibitor can be selected from, but is not limited to, one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, trans-zeatin, AZD0364, usnic acid, ASTX-029, VX-11e, notoginsenoside R1, CC-90003, 2'S'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994). Because ERK is the only substrate of MEK, in some aspects, an ERK inhibitor can be an inhibitor of an element upstream of ERK, such as a MEK inhibitor. Examples of MEK inhibitors can be, but are not limited to, selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, R05126766, GDC-0623. Thus, also disclosed are methods of increasing sensitivity of a cancer cell to alternating electric fields comprising exposing the cancer cell to an alternating electric field for a period of time, the alternating electric field having a frequency and field strength, and exposing the cancer cell to an ERK inhibitor.

In some aspects, the disclosed methods of increasing treatment efficacy comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor in combination with a chemotherapeutic agent, an anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin).

In some aspects, the disclosed methods of increasing treatment efficacy comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor in combination with radiation therapy to the subject, wherein the result is an increase in cell susceptibility to DNA damage from the radiation therapy.

Disclosed are any of the above methods of increasing treatment efficacy or methods of treating a subject having cancer comprising applying an alternating electric field to a target site of the subject for a period of time, the alternating electric field having a frequency and field strength, wherein the target site comprises one or more cancer cells, and administering a therapeutically effective amount of one or more of IGF1R inhibitor, JNK inhibitor, RPS6 inhibitor, and/or ERK inhibitor to the subject, and further comprising administering a chemotherapeutic agent to the subject. In some aspects, a chemotherapeutic agent can be, but is not limited to, an alkylating agent, an antimetabolite agent, an antineoplastic antibiotic agent, and a mitotic inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the alternating electric fields. In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the IGFR1 inhibitor, JNK inhibitor, RPS6 inhibitor or ERK inhibitor.

D. METHODS OF REDUCING VIABILITY OF CANCER CELLS

Disclosed are methods of reducing viability of cancer cells comprising applying an alternating electric field to the cancer cells for a period of time, the alternating electric field having a frequency and field strength in combination with administering or exposing the cancer cell to one or more of an IGF1R inhibitor, JNK inhibitor, RPS6 inhibitor, and/or an ERK inhibitor.

Also disclosed are methods of reducing viability of cancer cells in a subject comprising applying an alternating electric field to the cancer cells for a period of time, the alternating electric field having a frequency and field strength in combination with administering to the subject one or more of anIGF1R inhibitor, JNK inhibitor, RPS6 inhibitor, and/or ERK inhibitor, and further comprising administering a chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) to the subject. In some aspects, a chemotherapeutic agent can be, but is not limited to, an alkylating agent, an antimetabolite agent, an antineoplastic antibiotic agent, and a mitotic inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the alternating electric fields. In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the IGFR1 inhibitor, JNK inhibitor, RPS6 inhibitor or ERK inhibitor.

Alternating Electric Field Plus Inhibitor

Disclosed are methods of reducing viability of cancer cells in a subject comprising applying an alternating electric field to a target site of the subject for a period of time, the alternating electric field having a frequency and field strength, wherein the target site comprises one or more cancer cells, and administering a therapeutically effective amount of one or more of an IGF1R inhibitor, JNK inhibitor, RPS6 inhibitor, and/or ERK inhibitor to the subject.

In some aspects, the one or more of the IGF1R inhibitor, JNK inhibitor, RPS6 inhibitor, and/or ERK inhibitor is administered prior to applying the alternating electric field. In some aspects, the one or more of the IGF1R inhibitor, JNK inhibitor, RPS6 inhibitor, and/or ERK inhibitor is administered after applying the alternating electric field. In some aspects, the one or more of the IGF1R inhibitor, JNK inhibitor, RPS6 inhibitor, and/or ERK inhibitor is administered simultaneously with applying the alternating electric field.

In some aspects, the cancer is a glioblastoma, ovarian, or lung metastatic carcinoma. In some aspects, the cancer can be any cancer.

In some aspects, the IGFR1 inhibitors can be, but are not limited to, antibodies, small molecules, oligonucleotides. In some aspects, the antibodies can be monoclonal antibodies against IFG1R or monoclonal antibodies against IFG1R ligand. In some aspects, the small molecules can be IGF1R tyrosine kinase inhibitors. In some aspects, the oligonucleotides can be antisense oligonucleotides, RNA interference, or circular RNA. In some aspects, the IGFR1 inhibitor can be selected from, but is not limited to, one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), 5961. Thus, disclosed are methods of reducing viability of cancer cells comprising exposing the cancer cell to an alternating electric field for a period of time, the alternating electric field having a frequency and field strength, and exposing the cancer cell to a IGF1R inhibitor.

In some aspects, the JNK inhibitors can be, but are not limited to, SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines. Thus, also disclosed are methods of reducing viability of cancer cells comprising exposing the cancer cell to an alternating electric field for a period of time, the alternating electric field having a frequency and field strength, and exposing the cancer cell to a JNK inhibitor.

In some aspects, an RPS6 inhibitor can be any composition or compound that inhibits RPS6, inhibits phosphorylation of RPS6, or inhibits phosphorylated RPS6. In some aspects, a RPS6 inhibitor can be, a shRNA. In some aspects, a RPS6 inhibitor can be an mTOR inhibitor, wherein mTOR inhibitors act as a dephosphorylator of RPS6. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D and TML-6. In some aspects, a RPS6 inhibitor can be an AKT inhibitor, wherein AKT inhibitors act can prevent RPS6 phosphorylation. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f] [1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, or NSC781406. Thus, also disclosed are methods of reducing viability of cancer cells comprising exposing the cancer cell to an alternating electric field for a period of time, the alternating electric field having a frequency and field strength, and exposing the cancer cell to a RPS6 inhibitor.

In some aspects, the ERK inhibitor can be selected from, but is not limited to, one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, trans-zeatin, AZD0364, usnic acid, ASTX-029, VX-11e, notoginsenoside R1, CC-90003, 2'S'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994). Because ERK is the only substrate of MEK, in some aspects, an ERK inhibitor can be an inhibitor of an element upstream of ERK, such as a MEK inhibitor. Examples of MEK inhibitors can be, but are not limited to, selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, R05126766, GDC-0623. Thus, also disclosed are methods of reducing viability of cancer cells comprising exposing the cancer cell to an alternating electric field for a period of time, the alternating electric field having a frequency and field strength, and exposing the cancer cell to an ERK inhibitor.

E. METHODS OF INCREASING APOPTOSIS

Disclosed are methods of increasing apoptosis of a cancer cell comprising exposing the cancer cell to an alternating electric field for a period of time, the alternating electric field having a frequency and field strength; and exposing the cancer cell to an IGFR1 inhibitor, JNK inhibitor, RPS6 inhibitor or ERK inhibitor.

In some aspects, the IGFR1 inhibitors can be, but are not limited to, antibodies, small molecules, oligonucleotides. In some aspects, the antibodies can be monoclonal antibodies against IFG1R or monoclonal antibodies against IFG1R ligand. In some aspects, the small molecules can be IGF1R tyrosine kinase inhibitors. In some aspects, the oligonucleotides can be antisense oligonucleotides, RNA interference, or circular RNA. In some aspects, the IGFR1 inhibitor can be selected from, but is not limited to, one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), 5961. Thus, disclosed are methods of increasing apoptosis of a cancer cell comprising exposing the cancer cell to an alternating electric field for a period of time, the alternating electric field having a frequency and field strength, and exposing the cancer cell to a IGF1R inhibitor.

In some aspects, the JNK inhibitors can be, but are not limited to, SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines. Thus, also disclosed are methods of increasing apoptosis of a cancer cell comprising exposing the cancer cell to an alternating electric field for a period of time, the alternating electric field having a frequency and field strength, and exposing the cancer cell to a JNK inhibitor.

In some aspects, an RPS6 inhibitor can be any composition or compound that inhibits RPS6, inhibits phosphorylation of RPS6, or inhibits phosphorylated RPS6. In some aspects, a RPS6 inhibitor can be, a shRNA. In some aspects, a RPS6 inhibitor can be an mTOR inhibitor, wherein mTOR inhibitors act as a dephosphorylator of RPS6. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D and TML-6. In some aspects, a RPS6 inhibitor can be an AKT inhibitor, wherein AKT inhibitors act can prevent RPS6 phosphorylation. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f] [1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, or NSC781406. Thus, also disclosed are methods of increasing apoptosis of a cancer cell comprising exposing the cancer cell to an alternating electric field for a period of time, the alternating electric field having a frequency and field strength, and exposing the cancer cell to a RPS6 inhibitor.

In some aspects, the ERK inhibitor can be selected from, but is not limited to, one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, trans-zeatin, AZD0364, usnic acid, ASTX-029, VX-11e, notoginsenoside R1, CC-90003, 2'S'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994). Because ERK is the only substrate of MEK, in some aspects, an ERK inhibitor can be an inhibitor of an element upstream of ERK, such as a MEK inhibitor. Examples of MEK inhibitors can be, but are not limited to, selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, R05126766, GDC-0623. Thus, also disclosed are methods of increasing apoptosis of a cancer cell comprising exposing the cancer cell to an alternating electric field for a period of time, the alternating electric field having a frequency and field strength, and exposing the cancer cell to an ERK inhibitor.

In some aspects, the alternating electric field and the IGFR1 inhibitor, JNK inhibitor, RPS6 inhibitor or ERK inhibitor are administered simultaneously. In some aspects, after simultaneous administration of alternating electric field and the IGFR1 inhibitor, JNK inhibitor, RPS6 inhibitor or ERK inhibitor, the IGFR1 inhibitor, JNK inhibitor, RPS6 inhibitor or ERK inhibitor is removed while the cancer cells remain exposed to the alternating electric field. In some aspects, even after the IGFR1 inhibitor, JNK inhibitor, RPS6 inhibitor or ERK inhibitor is removed, the increase in apoptosis of cancer cells remains.

Disclosed are any of the above methods of increasing apoptosis of a cancer cell comprising exposing the cancer cell to an alternating electric field for a period of time, the alternating electric field having a frequency and field strength; and exposing the cancer cell to an IGFR1 inhibitor, JNK inhibitor, RPS6 inhibitor or ERK inhibitor and further comprising exposing the cell to a chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin). In some aspects, a chemotherapeutic agent can be, but is not limited to, an alkylating agent, an antimetabolite agent, an antineoplastic antibiotic agent, and a mitotic inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the alternating electric fields. In some aspects, the chemotherapeutic agent, anticancer drug, a cytotoxic drug, pain-management drug, *pseudomonas* exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin) can be administered prior to, simultaneously with or after the IGFR1 inhibitor, JNK inhibitor, RPS6 inhibitor or ERK inhibitor.

F. ALTERNATING ELECTRIC FIELDS

The methods disclosed herein comprise alternating electric fields. In some aspects, the alternating electric field used in the methods disclosed herein is a tumor-treating field (TTFields). In some aspects, the alternating electric field can vary dependent on the type of cell or condition to which the alternating electric field is applied. In some aspects, the alternating electric field can be applied through one or more electrodes placed on the subject's body. In some aspects, there can be two or more pairs of electrodes. For example, arrays can be placed on the front/back and sides of a patient and can be used with the systems and methods disclosed herein. In some aspects, where two pairs of electrodes are used, the alternating electric field can alternate between the pairs of electrodes. For example, a first pair of electrodes can be placed on the front and back of the subject and a second pair of electrodes can be placed on either side of the subject, the alternating electric field can then be applied and can alternate between the front and back electrodes and then to the side to side electrodes.

In some aspects, the frequency of the alternating electric field is between 100 and 500 kHz. The frequency of the alternating electric fields can also be, but is not limited to, between 50 and 500 kHz, between 100 and 500 kHz, between 25 kHz and 1 MHz, between 50 and 190 kHz, between 25 and 190 kHz, between 180 and 220 kHz, or between 210 and 400 kHz. In some aspects, the frequency of the alternating electric fields can be electric fields at 50 kHz, 100 kHz, 200 kHz, 300 kHz, 400 kHz, 500 kHz, or any frequency between. In some aspects, the frequency of the alternating electric field is from about 200 kHz to about 400 kHz, from about 250 kHz to about 350 kHz, and may be around 300 kHz.

In some aspects, the field strength of the alternating electric fields can be between 1 and 4 V/cm RMS. In some aspects, different field strengths can be used (e.g., between 0.1 and 10 V/cm). In some aspects, the field strength can be 1.75 V/cm RMS. In some embodiments the field strength is at least 1 V/cm. In other embodiments, combinations of field strengths are applied, for example combining two or more frequencies at the same time, and/or applying two or more frequencies at different times.

In some aspects, the alternating electric fields can be applied for a variety of different intervals ranging from 0.5 hours to 72 hours. In some aspects, a different duration can be used (e.g., between 0.5 hours and 14 days). In some aspects, application of the alternating electric fields can be repeated periodically. For example, the alternating electric fields can be applied every day for a two-hour duration.

In some aspects, the exposure may last for at least 6 hours, at least 12 hours, at least 24 hours, at least 36 hours, at least 48 hours, or at least 72 hours or more.

G. KITS

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits for treating cancer. In some aspects, the kit can comprise equipment for applying alternating electrical fields.

Also disclosed are kits comprising a system or equipment for administering alternating electrical fields and one or more of the disclosed IGFR1 inhibitors, JNK inhibitors, RPS6 inhibitors or ERK inhibitors.

Disclosed are kits comprising a device capable of administering an alternating electric field and optionally one or more of the disclosed IGFR1 inhibitors, JNK inhibitors, RPS6 inhibitors or ERK inhibitors. Disclosed are kits comprising a device capable of administering an alternating electric field and optionally one or more of the disclosed IGFR1 inhibitors, JNK inhibitors, RPS6 inhibitors or ERK inhibitors. In some aspects, the kits further comprise instructions for using the device.

In some aspects the kits disclosed herein can further comprise instructions for using a device capable of administering an alternating electric field in combination with one or more of the disclosed IGFR1 inhibitors, JNK inhibitors, RPS6 inhibitors or ERK inhibitors.

In some aspects, the kits disclosed herein can comprise instructions for where to apply the alternating electrical field. In some aspects, the kits disclosed herein can comprise instructions for determining a region-of-interest (ROI) within a 3D model of a portion of a subject's body, determining, based on a center of the ROI, a plane that transverses the portion of the subject's body, wherein the plane comprises a plurality of pairs of positions along a contour of the plane, adjusting, based on an anatomical restriction, one or more positions of the plurality of pairs of positions to generate a modified plane, determining, for each pair of positions of the plurality of pairs positions on the modified plane, a simulated electric field distribution, determining, based on the simulated electric field distributions, a dose metric for each pair of positions of the plurality of pairs positions, determining one or more sets of pairs of positions of the plurality of pairs of positions that satisfy an angular restriction between pairs of transducer arrays, and determining, based on the dose metrics and the one or more sets of pairs of positions that satisfy the angular restriction, one or more candidate transducer array layout maps.

In some aspects, the kits disclosed herein comprise a device capable of administering an alternating electric field comprises electrodes for applying the alternating electric field. (e.g. Optune system). In some aspects, the kits disclosed herein can further comprise instructions on where to apply the electrodes to increase the efficacy of alternating electric fields therapy. In some aspects, the kits disclosed herein further comprise instructions for conducting and analyzing measurements to determine where to apply the electrodes or where to apply the alternating electrical field.

H. EMBODIMENTS

Embodiment 1: A method of increasing sensitivity of a cancer cell to alternating electric fields comprising: (A) exposing the cancer cell to an alternating electric field for a period of time, the alternating electric field having a frequency and field strength, and (B) exposing the cancer cell to an IGFR1 inhibitor, JNK inhibitor, RPS6 inhibitor or ERK inhibitor.

Embodiment 2: The method of any preceding embodiment, wherein the frequency of the alternating electric field is between 100 and 500 kHz.

Embodiment 3: The method of any preceding embodiment, wherein the frequency of the alternating electric field is between 180 and 220 kHz.

Embodiment 4: The method of any preceding embodiment, wherein the cancer cell is a glioblastoma cell, ovarian cell, or lung metastatic carcinoma cell.

Embodiment 5: The method of any preceding embodiment, wherein the cancer cell is in a subject.

Embodiment 6: The method of any preceding embodiment, wherein the cancer cells are exposed to the alternating electric field and IGFR1 inhibitor, JNK inhibitor, RPS6 inhibitor or ERK inhibitor simultaneously.

Embodiment 7: The method of any preceding embodiment, wherein the IGFR inhibitor is selected from one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), and 5961.

Embodiment 8: The method of any preceding embodiment, wherein the JNK inhibitor is selected from one or more of the group consisting of: SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylamino-hexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines.

Embodiment 9: The method of any preceding embodiment, wherein the RPS6 inhibitor is selected from one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D, TML-6. lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, and NSC781406.

Embodiment 10: The method of any preceding embodiment, wherein the ERK inhibitor is selected from one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, transzeatin, AZD0364, usnic acid, ASTX-029, VX-11e, notoginsenoside R1, CC-90003, 2'5'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994), selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, R05126766, or GDC-0623.

Embodiment 11: A method of treating a subject having cancer comprising (A) applying an alternating electric field to a target site of the subject for a period of time, the alternating electric field having a frequency and field strength, wherein the target site comprises one or more cancer cells, and (B) administering a therapeutically effective amount of an IGFR1 inhibitor, JNK inhibitor, RPS6 inhibitor or ERK inhibitor to the subject.

Embodiment 12: A method of reducing viability of a cancer cell in a subject comprising (A) applying an alternating electric field to a target site of the subject for a period of time, the alternating electric field having a frequency and field strengthwherein the target site comprises one or more cancer cells, and (B) administering a therapeutically effective amount of an IGFR1 inhibitor, JNK inhibitor, RPS6 inhibitor or ERK inhibitor to the subject.

Embodiment 13: The method of embodiments 11-12, wherein the IGFR1 inhibitor, JNK inhibitor, RPS6 inhibitor or ERK inhibitor is administered prior to applying the alternating electric field.

Embodiment 14: The method of embodiments 11-12, wherein the IGFR1 inhibitor, JNK inhibitor, RPS6 inhibitor or ERK inhibitor is administered after applying the alternating electric field.

Embodiment 15: The method of embodiments 11-12, wherein the IGFR1 inhibitor, JNK inhibitor, RPS6 inhibitor or ERK inhibitor is administered simultaneously with applying the alternating electric field.

Embodiment 16: The method of embodiments 11-16, wherein the alternating electric field increases expression of IGF1R, JNK, RPS6, or ERK in the one or more cancer cells.

Embodiment 17: The method of embodiments 11-16, wherein the cancer is glioblastoma, ovarian, or lung metastatic carcinoma.

Embodiment 18: The method of embodiments 11-17, wherein the IGFR1 inhibitor is selected from one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), 5961.

Embodiment 19: The method of embodiments 11-18, wherein the JNK inhibitor is selected from one or more of the group consisting of: SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4, 40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines.

Embodiment 20: The method of embodiments 11-19, wherein the RPS6 inhibitor is selected from one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D, TML-6. lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 4 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, and NSC781406.

Embodiment 21: The method of embodiments 11-20, wherein the ERK inhibitor is selected from one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, trans-zeatin, AZD0364, usnic acid, ASTX-029, VX-11e, notoginsenoside R1, CC-90003, 2'5'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994), selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, RO5126766, and GDC-0623.

Embodiment 22: The method of embodiments 11-21, wherein the frequency is between 100 and 500 kHz.

Embodiment 23: The method of embodiment 22, wherein the frequency is between 180 and 220 kHz.

Embodiment 24: A method of increasing apoptosis of a cancer cell comprising (A) exposing the cancer cell to an alternating electric field for a period of time, the alternating electric field having a frequency and field strength; and (B) exposing the cancer cell to an IGFR1 inhibitor, JNK inhibitor, RPS6 inhibitor or ERK inhibitor.

Embodiment 25: The method of embodiment 24, wherein the alternating electric field and the IGFR1 inhibitor, JNK inhibitor, RPS6 inhibitor or ERK inhibitor are administered simultaneously.

Embodiment 26: The method of embodiment 25, wherein after simultaneous administration of alternating electric field and the IGFR1 inhibitor, JNK inhibitor, RPS6 inhibitor or ERK inhibitor the IGFR1 inhibitor, JNK inhibitor, RPS6 inhibitor or ERK inhibitor is removed while the cancer cells remain exposed to the alternating electric field.

Embodiment 27: The method of embodiments 24-26, wherein even after the IGFR1 inhibitor, JNK inhibitor, RPS6 inhibitor or ERK inhibitor is removed, the increase in apoptosis of cancer cells remains.

Embodiment 28: The method of embodiments 24-27 wherein the IGFR1 inhibitor is selected from one or more of the group consisting of: cixutumumab (IMC-A12), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), and 5961.

Embodiment 29: The method of embodiments 24-25, wherein the JNK inhibitor is selected from one or more of the group consisting of: SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4, 40-bipyridines, isoxazole derivatives, XG-102, 4-quinolone analog 13c, 4-phenylisoquinolone 11g, ginsenoside Rg1, and pyridopyrimidinone derivatives. JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines.

Embodiment 30: The method of embodiments 24-29, wherein the RPS6 inhibitor is selected from one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D, TML-6. lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, Scutellarin, GNE-317, GNE-403, and NSC781406.

Embodiment 31: The method of embodiments 24-30, wherein the ERK inhibitor is selected from one or more of the group consisting of: BVD-523, CC-90003, GDC-0094, cobimetinib, MK-8353, bosutinib, BIX 02189, resveratrol, SCH772984, hypaphorine, KO-947, urolithin B, SEA0400, loureirin B, ezatiostat, tracheloside, MRTX-1257, falcarindiol, HI-TOPK-032, cucurbitacin IIb, BAY-885, DEL-22379, Astragaloside IV, TIC10, MK-8353, trans-zeatin, AZD0364, usnic acid, ASTX-029, VX-11e, notoginsenoside R1, CC-90003, 2'5'-dihydroxyacetophenone, mulberroside A, ERK5-IN-1, magnolin, XMD8-92, LY3214996, pluripotin (SC1), ulixertinib (BVD-523), methylthiouracil, adjudin, FR 180204, AG-126, corynoxeine, ERK5-IN-2, ravoxertinib (GCD-0994), selumetinib, mirdametinib, trametinib, U0126-EtOH, PD184352, trametinib DM SO solvate, PD98059, BIX 02189, pimasertib, pelitinib, BIX 02188, TAK-733, AZD8330, binimetinib, PD318088, honokiol, SL-327, refametinib, myricetin, BI-847325, cobimetinib, RO5126766, or GDC-0623.

Embodiment 32: The method of embodiments 1, 11, or 12, further comprising administering a chemotherapeutic agent to the subject.

Embodiment 33: The method of embodiments 24-32, further comprising exposing the cell to a chemotherapeutic agent.

EXAMPLES

Figure 2:
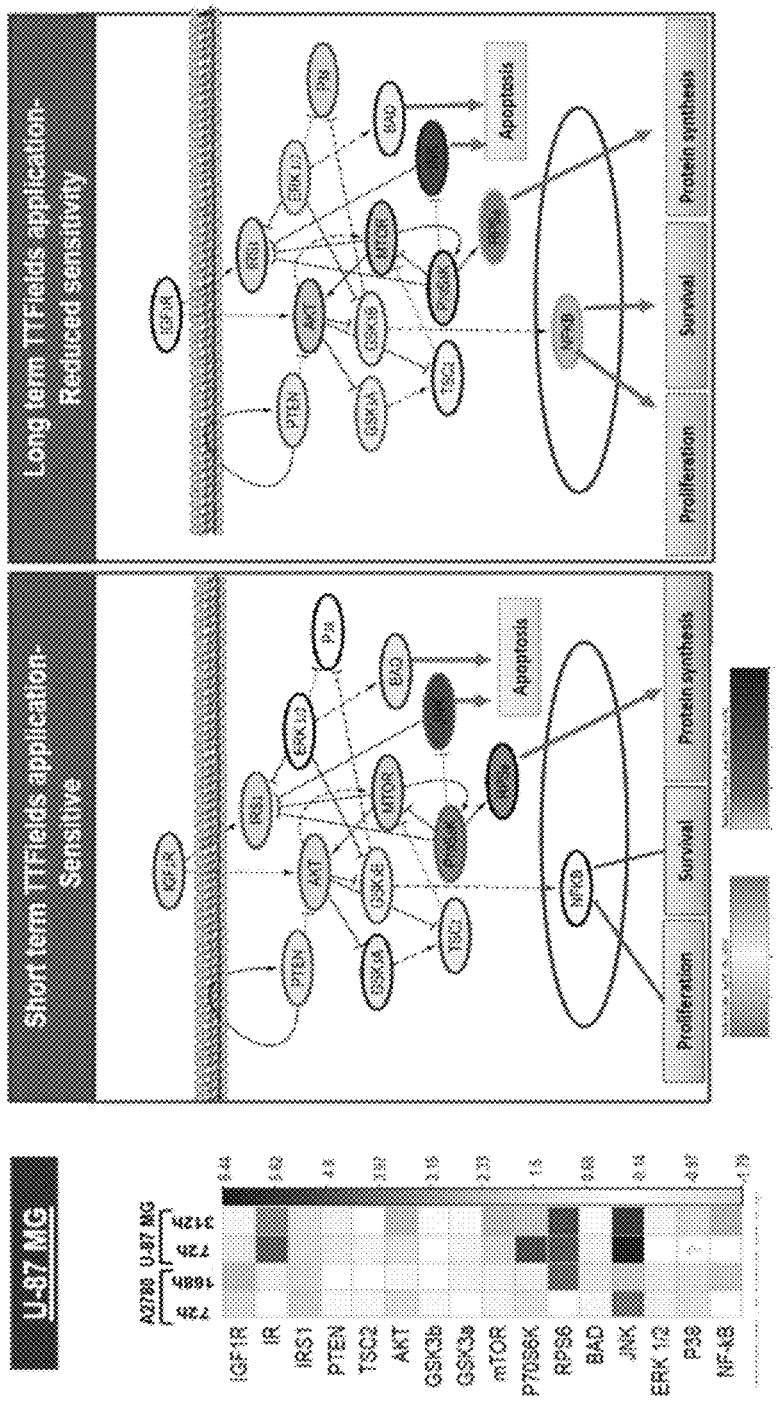
FIG. 2 is results from a Luminex analysis results showing changes in protein expression in U87 (glioblastoma cell line): Short term (left) is showing protein expression changes in TTFields following 72 hours compared with control samples results. Long term (right) is showing protein expression changes in TTFields following 312 hours compared with control samples results. Colors inside the circle-legend on the left bottom part of the figure—the darker colors towards the top of the scale show increase in expression, the lighter colors towards the bottom of the scale show a decrease in expression and no color shows no change. The surrounding lines of circles-legend on the right bottom part of the figure—the degree of statistically significant. Straight lines show a direct connection between proteins while dotted lines show an indirect connection.

As shown in FIGS. 1 and 2, a Luminex assay was performed to determine expression levels in response to TTFields. Based on these results proteins that were statistically significant and also showed the same trend in both cell lines were chosen to focus on. IGF1R is upregulated. IRS is downregulated but activation of IRS1 can be dangerous since it has many effects of cell signaling. JNK is upregulated. RPS6 is upregulated. Although ERK did not show a statistically significant change, ERK inhibition can be a good option because it is a parallel pathway to JNK. NFkB is upregulated but altering expression can have detrimental effects. Based on these results, inhibition of IGF1R, JNK, ERK, and RPS6 were chosen to inhibit.

Figures 3A, 3B:
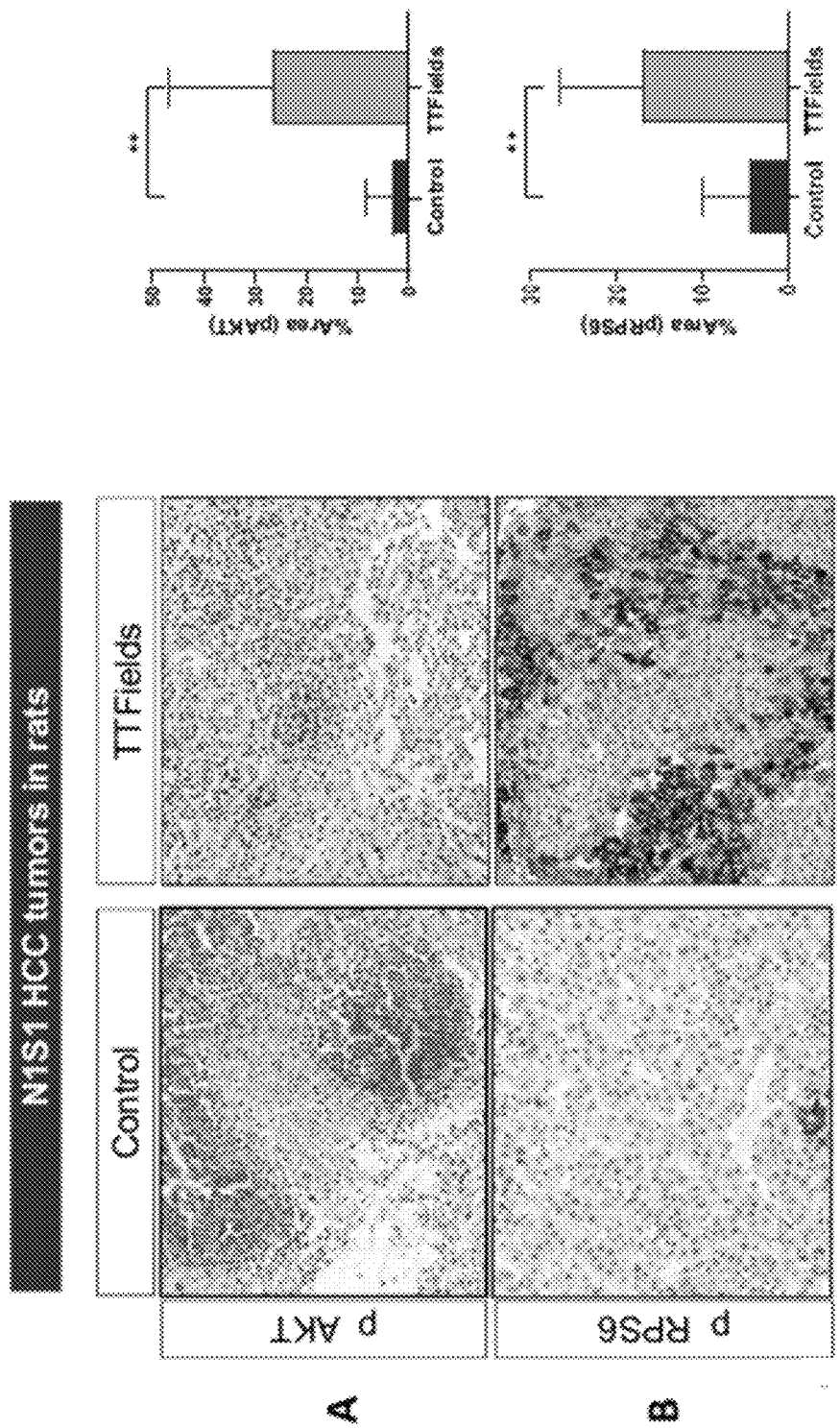
FIG. 3A and FIG. 3B show the application of TTFields activates AKT (A) and RPS6 (B) phosphorylation in vivo.

FIG. 3 shows immunohistochemistry (IHC) and western blot results showing that RSP6 is increased following TTFields.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of increasing sensitivity of a cancer cell to alternating electric fields comprising:
   a. exposing the cancer cell to an alternating electric field for a period of time, the alternating electric field having a frequency and field strength, and
   b. exposing the cancer cell to an IGFR1 inhibitor or JNK inhibitor.

2. The method of claim 1, wherein the frequency of the alternating electric field is between 100 and 500 kHz.

3. The method of claim 2, wherein the frequency of the alternating electric field is between 180 and 220 kHz.

4. The method of claim 1, wherein the cancer cell is a glioblastoma cell, ovarian cell, or lung metastatic carcinoma cell.

5. The method of claim 1, wherein the cancer cell is in a subject.

6. The method of claim 1, wherein the cancer cells are exposed to the alternating electric field and IGFR1 inhibitor, JNK inhibitor, RPS6 inhibitor or ERK inhibitor simultaneously.

7. The method of claim 1, wherein the IGFR1 inhibitor is selected from one or more of the group consisting of: cixutumumab (IMC-Al2), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), and 5961.

8. The method of claim 1, wherein the JNK inhibitor is selected from one or more of the group consisting of: SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives, JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines.

9. A method of treating a subject having cancer comprising:
   (a) applying an alternating electric field to a target site of the subject for a period of time, the alternating electric field having a frequency and field strength, wherein the target site comprises one or more cancer cells, and
   (b) administering a therapeutically effective amount of an IGFR1 inhibitor or JNK inhibitor to the subject.

10. A method of reducing viability of a cancer cell in a subject comprising:

(a) applying an alternating electric field to a target site of the subject for a period of time, the alternating electric field having a frequency and field strength, wherein the target site comprises one or more cancer cells, and (b) administering a therapeutically effective amount of an IGFR1 inhibitor or JNK inhibitor to the subject.

11. The method of 9, wherein the cancer is glioblastoma, ovarian, or lung metastatic carcinoma.

12. The method of claim 9, wherein the IGFR1 inhibitor is selected from one or more of the group consisting of: cixutumumab (IMC-Al2), Figitumumab (CP-751, 871), Dalotuzumab (MK-0646; h7C10), Ganitumab (AMG 479), R1507, SCH 717454 (19D12), AVE1642 (EM164), BIIB022, MEDI-573, Linsitinib (OSI-096), BMS-754807, BVP 51004, XL228, INSM-18 (NDGA), NVP-AEW541, GSK1904529A, NVP-ADW742, BMS-536924, Ceritinib (LDK378), AG-1024, GSK1838705A, SBI-477, PQ 401, AZD3463, NT157, Brigatinib (AP26113), Picropodophyllin (PPP), 5961.

13. The method of claim 9, wherein the JNK inhibitor is selected from one or more of the group consisting of: SP600125, AS601245, N-(3-cyano-4,5,6,7-tetrahydro-1-benzothien-2-yl)amides, azaquinolone analog168 and N-alkyl (propyl and butyl)-bearing pyrazoloanthrone scaffolds, 7-(6-N-phenylaminohexyl)amino-2H-anthra[1,9-cd]pyrazol-6-one, HCC or Bi-78D3, PYC98, PYC71N, adamantyl azaquinolone, Pyrimidinyl-substituted benzazole-acetonitriles, 6-anilinoindazoles, 20-anilino-4,40-bipyridines, isoxazole derivatives, XG-102, 4-quinolone analog 13c, 4-phenylisoquinolone 11g, ginsenoside Rg1, and pyridopyrimidinone derivatives, JNK-IN-1 to JNK-IN-12, IRAK1, PIK3C3, PIP4K2C, PIP5K3, anthrapyrazolone, indazoles, aminopyrazoles, aminopyridines, pyridine carboxamides, benzothien-2-ylamides and benzothiazol-2-yl acetonitriles, quinoline derivatives, and aminopyrimidines.

14. The method of claim 1, wherein the frequency is between 100 and 500 kHz.

15. The method of claim 14, wherein the frequency is between 180 and 220 kHz.

* * * * *